United States Patent [19]

Tabaeizadeh et al.

[11] Patent Number: 5,656,474
[45] Date of Patent: Aug. 12, 1997

[54] **ENDOCHITINASE GENE INDUCED BY OSMOTIC STRESS AND ABSCISIC ACID ISOLATED FROM THE WILD TOMATO *LYCOPERSICON CHILENSE* DUN**

[75] Inventors: Zohreh Tabaeizadeh, Westmount; Long-Xi Yu, Montreal, both of Canada; Ri-Dong Chen, St. Paul, Minn.

[73] Assignee: Universite du Quebec a Montreal (UQAM), Canada

[21] Appl. No.: 162,475

[22] Filed: Dec. 7, 1993

[51] Int. Cl.$^6$ .............................. C12N 9/44; C12N 15/56
[52] U.S. Cl. .................... 435/209; 435/252.3; 435/320.1; 435/172.3; 536/23.2
[58] Field of Search .............................. 435/209, 252.3, 435/320.1, 172.3; 536/23.2

[56] References Cited

PUBLICATIONS

GenBank entry M97210, (Jun. 7, 1993).
M.H.A.J. Joosten et al., "Identification of Several Pathogenesis–Related Proteins in Tomato Leaves Inoculated with *Cladosporium–fulvum* as 1,3–β–Glucanases and Chitinases", 89(3) 945–951, (1989).
N. Danhash et al., "Molecular Characterization of Four Chitinase cDNAs Obtained From *Cladosporium–fulvum*–Infected Tomato", 22(6) 1017–1029 (Sep. 1993).
Baker, J. et al. (1988). Plant Molecular Biology. 11: 277–291.
Boller, T. (1988). Oxford Surveys of Plant Molecular & Cell Biology 5: 145–174.
Bray, E.A. (1988). Plant Physiol. 88: 1210–1214.
Chen, R.D. and Tabaeizadeh, Z. (1992a). Genome 35: 385–391.
Chen, R.–D. and Tabaeizadeh, Z. (1992b). Biochem. Cell Biol. 70: 199–206.
Chen, R.–D. et al. (1993). Plant Physiol. 103: 301.
Clarke, J.M. and Durley, R.C. (1981). "The Response of Plants to Drought Stress" *In Water Stress on Plants*, (Simpson, G.M., ed.) Praeger, New York, pp. 89–139.
Devereux, J. et al. (1984). Nucleic Acids Research. 12(1): 387–391.
Fisher, R.A. and Turner, N.C. (1978). Ann. Rev. Plant Physiol. 29:277–317.
Gaynor, J.J. (1988). Nucleic Acids Research: 16(11): 5210.
Gómez, J. et al. (1988). Nature. 334: 262–264.
Greer, A.F. and Tabaeizadeh, Z. (1991). Can. J. Bot. 69: 2257–2260.
Hanson, A.D. and Hitz, W.D. (1982). Ann. Rev. Plant Physiol. 33: 163–203.
Leah, R. et al. (1991). Journal of Biological Chemistry. 266(25): 1564–1573.
Maniatis, T. et al. (1982). *Molecular Cloning: A laboratory Manual* (Cold Spring Harbor Laboratory, Cold Spring Harbor, NY).
Mauch, F. et al. (1988). Plant Physiol. 88: 936–942.
Memelink, J. et al. (1990). Plant Molecular Biology. 14: 119–126.
Metraux, J.P. (1989). Proc. Natl. Acad. Sci. USA. 86: 896–900.
Mundy, J. and Chua, N.–H. (1988). EMBO Journal 7(8): 2279–2286.
Neale, A. D. et al. (1990). The Plant Cell. 2: 673–684.
Parent, J.–G. et al. (1985). Can. J. Bot. 63: 928–931.
Payne, G. et al. (1990). Proc. Natl. Acad. Sci. USA. 87: 98–102.
Sachs, M.M. and HO, T.–H. D. (1986), Ann. Rev. Plant Physiol. 37: 363–376.
Sanger, F. et al. (1977). Proc. Natl. Acad, Sci. USA. 74(12): 5463–5467.
Schlumbaum, A. et al. (1986). Nature. 324:365–367.
Skriver, K. and Mundy, J. (1990). The Plant Cell. 2: 503–512.
Shinshi, H. et al. (1990) Plant Molecular Biology. 14: 357–368.
Simpson, G.M. (1981). "The Value of Physiological Knowledge of Water Stress in Plants", *In Water Stress on Plants*, (Simpson, G.M., Ed), Praeger, NY, pp. 235–265.
Trudel, J. and Asselin, A. (1989). Analytical Biochemistry. 178: 362–366.
Ward, E. R. et al. (1991). The Plant Cell. 3: 1085–1094.
Wu, M.M.J., et al. (1983). Current Genetics. 7: 385–392.

*Primary Examiner*—Charles L. Patterson, Jr.
*Assistant Examiner*—Rebecca Prouty
*Attorney, Agent, or Firm*—Cushman Darby & Cushman, IP Group of Pillsbury Madison & Sutro, L.L.P.

[57] ABSTRACT

Two osmotic stress- and ABA-responsive members of the endochitinase (EC 3.2.1.14) gene family has been isolated and identified from leaves of drought-stressed *Lycopersicon chilense* plants. The 966-base-pair insert of pcht28 encodes an acidic chitinase precursor with an amino-terminal signal peptide. The mature protein is predicted to have 229 amino acid residues with a relative molecular weight of 24,943 and pI value of 6.2. The same number in amino acids, molecular and PI value are predicted for the protein encoded by pchtI, despite of a slight variation in the DNA and amino acid sequences. Sequence analysis revealed that pcht28 and pchtI have a high degree of homology with class II chitinases (EC 3.2.1.14) from tobacco. Northern blot analysis indicated that these genes have evolved a completely different pattern of expression from others reported thus far. They are highly induced by both osmotic stress and the plant hormone abscisic acid. Southern blot analysis of genomic DNA suggested that the pcht28- and pchtI-related chitinase is encoded by a small multigene family in this species. Knowing the role of plant chitinase in plant defense against fungal pathogens, it is assumed that, besides their general defensive function, the pcht28- and pchtI-encoded chitinases may play a particular role in protecting plants from pathogen attack during water stress.

1 Claim, 6 Drawing Sheets

```
                                    ↓
GTTAAAAAGCCAGAGGAAAAATGAAGTTCAATATTGTATCACCAGTTGCACTGTCTTGTC        60
                  M  K  F  N  I  V  S  P  V  A  L  S  C  L        14

TCTTTTTCTTGTTCCTAACAGGTACTTTAGCACAAAATGCCGGTTCCATTGTAACGCGGG       120
 F  F  L  F  L  T  G  T  L  A  Q  N  A  G  S  I  V  T  R  E       34

AATTGTTCGAACAAATGCTGAGTTTTAGGAACAATGACGCATGTCCTGCCAAAGGATTCT       180
 L  F  E  Q  M  L  S  F  R  N  N  D  A  C  P  A  K  G  F  Y       54

ACACTTATGATGCATTCATAGCTGCAGCCAATTCGTTTCCAGGTTTTGGTACTACTGGTG       240
 T  Y  D  A  F  I  A  A  A  N  S  F  P  G  F  G  T  T  G  D       74

ATGATACTGCACGTAAGAAGGAAATTGCTGCCTTTTTCGGTCAAACATCTCATGAAACTA       300
 D  T  A  R  K  K  E  I  A  A  F  F  G  Q  T  S  H  E  T  K       94
                                                       (N)
 T
AGGGTGGTAGTGCAGGAACATTCACTGGAGGATATTGCTTTGTTAGGCAAATAGATCAGT       360
 G  G  S  A  G  T  F  T  G  G  Y  C  F  V  R  Q  I  D  Q  S      114

CAGACAGATACTATGGCAGAGGACCTATCCAATTGACACACCAATCTAACTACGAACGAG       420
 D  R  Y  Y  G  R  G  P  I  Q  L  T  H  Q  S  N  Y  E  R  A      134

CTGGACAAGGTATTGGTGTTGGACAAGACTTAGTGAACAACCCTGATTTAGTTGCGACAG       480
 G  Q  G  I  G  V  G  Q  D  L  V  N  N  P  D  L  V  A  T  D      154

A                                  CC
ATCCTATAATATCATTCAGAACAGCAATATGGTTCTGGATGACAGCACAGGATAATAAAC       540
 P  I  I  S  F  R  T  A  I  W  F  W  M  T  A  Q  D  N  K  P      174
             (K)                       (H)(H)

CATCATGCCACAACGTTATCATTGGACAATGGACGCCATCCCCTGCAGATACGGCAGCTA       600
 S  H  N  V  I  I  G  Q  W  T  P  S  P  A  D  T  A  A  N        194

ATAGAGTTCCAGGGTACGGTGTCATTACCAACATCATTAACGGTGGACTTGAATGTAATA       660
 R  V  P  G  Y  G  V  I  T  N  I  I  N  G  G  L  E  C  N  M     214

TGGGTCCAAATACTGCAGTGGAAAGTCGAATTGGATTTTACAGGAGGTATTGTGGTATGT       720
 G  P  N  T  A  V  E  S  R  I  G  F  Y  R  R  Y  C  G  M  L     234

TGAATGTTCCTACTGGTGAAAAATTTGGACTGTAACAATCAAAAGAACTTCGCCCAGGCT       780
 N  V  P  T  G  E  N  L  D  C  N  N  Q  K  N  F  A  Q  G  *     256

A
AAGCGTCTTTATATATAGAGAGAATGCAAATTATGTTTATGTATTACGTTGTGAAGTCTA       840

TAAGTTATATTTGGATGTAATCAATAAGGGGATTCTGTATGCCCATTTAGAAAAATGGAA       900
          A                        -  A    -
GTTGATTTTCAGAAATACTAAAGTTATATGATTTTGATAC-TTTTGTTATAAAAAAAAAA       959

AAAAAAA                                                          966
```

Fig. 1

```
MKFNIUSPURLSCLFFLFLTGTLAQHAGSIUTRELFEQMLSFRNNOACPRKGFYTYDRFI    L.chilense
MEFSGSPMALFCCUFFLFLTGSLAQGIGSIUTSDLFMEMLKNRNDGRCPANGFYTYDRFI    N.tabacum 100
ARANSFPGFGTTGDDTARRKEIRAFFGQTSHETKGG--SAGTFTGGYCFURQIDQSDRYY    L.chilense
ARANSFPGFGTTGDDTARRKEIRAFFGQTSHETTGGSLSREPFTGGYCFURQNDQSDRYY    N.tabacum 150
GRGPIQLTMQSNVERAGQGIGUGQDLUNMPDLURTDPIISFRTAIMFUMTRQDNKPSCMN    L.chilense
GRGPIQLTMRNNYEKRGTRI--GQELUNMPDLURTDRTISFKTRIMFUMTPQDNKPSSMD    N.tabacum 200
UIIGNTPSPRGTRANRUPSYGUITMIINGQLECNMSPNTRUESRIGFVRRYCGMLHUPT    L.chilense
UIIGNTPSANDTRANRUPSYGUITMIINGQIECSIRNDRUEDRIGYVRRYCGMLHURP    N.tabacum 253
SEMLDCNNONPACP                                                  L.chilense
SEMLDCNNONPACP                                                  N.tabacum
```

Fig. 2

ENDOCHITINASE GENE INDUCED BY OSMOTIC STRESS AND ABSCISIC ACID ISOLATED FROM THE WILD TOMATO *LYCOPERSICON CHILENSE* DUN

BACKGROUND OF THE INVENTION

Water deficit is one of the most widespread environmental stresses limiting plant productivity and distribution (Fisher and Turner, 1978). However, depending on their level of resistance, many plant species can successfully cope with varying degrees of drought by modifying their morphological, physiological and metabolic processes (Clark and Durley, 1981; Hanson and Hitz, 1982). It is believed that the altered phenotype of plants with an enhanced ability to survive and grow under environmental stresses is largely the result of changes in gene expression (Sachs and Ho, 1986). Indeed, It has been well documented that plant adaptive responses to water stress are accompanied by the accumulation of specific mRNAs (Bray, 1988; Chen and Tabaeizadeh, 1992a,b). The changes in gene expression can also be partly induced by application of exogenous abscisic acid (Bray, 1988; Chen and Tabaeizadeh, 1992a,b), the plant hormone which appears to modulate the response of plants to water-stress (Skriver and Mundy, 1990). During the last few years, a number of drought- and ABA-responsive genes have been isolated and characterized from several species (Baker et al., 1988; Mundy and Chua, 1988; Gomez et al., 1988; Skriver and Mundy, 1990; Chen et al., 1993). These gene products may protect cells from damage at low water potentials (Baker et al., 1988).

STATEMENT OF THE INVENTION

We have isolated several drought- and ABA-induced cDNA clones from the wild tomato *Lycopersicon chilense* (Chen and Tabaeizadeh, 1992a), a natural inhabitant of extremely arid regions in South America (Rick, 1983). Here is described the characterization of two of these clones, pchtI and pcht28. They were identified to encode acidic endochitinase (EC 3.2.1.14, chitinase). Purified chitinases have shown the inhibition of fungal growth (Schlumbaum et al., 1986; Mauch et al., 1988). A direct role of endochitinase in plant defense against fungal infection (Boller, 1989; Collinge et al., 1993) has been suggested.

DESCRIPTION OF THE INVENTION

We were interested in understanding the molecular basis of drought resistance in *L. chilense*. In an attempt to investigate the role of drought and ABA-inducible genes, a cDNA library was obtained using poly(A) $^+$RNA prepared from leaves of plants which were drought-stressed for 4 days (Chen and Tabeizadeh, 1992b). By differential screening i.e. comparative to control plants, 8 clones were preferentially hybridized with the probes produced from drought- and ABA-treated plants and were first isolated (Chen and Tabeizadeh, 1992b). The sequence analysis showed that one of these clones, designated as pLC-15, was related to chitinase, sharing 77% amino acid sequence identity with the acidic chitinases PR-P and PR-Q from tobacco (Payne et al., 1990). Because the pLC-15 sequence was not a complete coding sequence, the same cDNA library was rescreened with $^{32}$P-labelled pLC15 in order to isolate a full-length cDNA clone. One of the positive clones, having the longest insert (designated as pchtI, for chitinase) was characterized. The sequence analysis showed that this clone was still a partial cDNA. Thus, a 5' fragment of pchtI insert was used as the probe to screen again the same library. The longest cDNA clone, designated as pcht28, contains an insert of approximately 970 base pairs (bp). It was revealed to be full-length after sequence analysis.

Drought results in many secondary adverse effects on plants. For example, plants under water stress often become more susceptible to various pathological diseases (Simpson, 1981). As a result, besides the direct induction of anti-dessication proteins, higher plants should have evolved drought-inducible defensive mechanisms against pathogen attack under this stressful environment. The pchtI and pcht28, drought-inducible chitinase genes, seem to be two of the examples.

In higher plants, chitinases are members of a group of proteins known as pathogenesis-related (PR) proteins that increase in response to pathogen infection (Boller, 1989). The alignment of the predicted amino acids from different plants indicated that there are at least three classes of endochitinases: Class I, basic chitinases with an N-terminal cysteine-rich domain and a highly conserved main structure; Class II, acidic proteins which are similar to class I chitinases but lack the cysteine-rich domain; and class III chitinases lack sequence similarity to class I or II enzymes and may be basic or acidic proteins (Shinshi et al., 1990). Different isoenzymes of chitinase have evolved completely different patterns of gene expression and are targeted to different subcellular locations. Class I chitinases are highly expressed in roots and basal leaves (Neale et al., 1990) and are induced by ethylene (Boller, 1988; Memelink et al., 1990). The mature enzyme appears to be localized primarily in the plant cell vacuole (Boller, 1988). Whereas, class II chitinases are expressed at low levels in different organs of healthy plants with flowers being the highest (Memelink et al., 1990). Ethylene has only a minor effect on their expression level. The enzymes are located extracellularly (Parent et al., 1988). Class III chitinases are induced by salicylic acid and the enzyme accumulates in the extracellular spaces of leaves (Metraux et al., 1989).

Analysis of the amino acid sequence suggests that the object of the present invention, pcht28 and pchtI proteins belong to class II chitinase. Our results show that these genes exhibit an organ-specific expression pattern in *L. chilense* plants. In contrast to the basic isoforms of class I, the encoded chitinase is undectable in roots but exhibits a high level in leaves. Moreover, we found that these members of the chitinase genes have evolved a novel regulation pattern, being highly inducible by osmotic stress. It is believed that the endogenous hormone ABA is involved in mediating the response of plants to osmotic stress. The data shown below demonstrate that application of exogenous ABA to plants allows to mimic the induction effect and strongly supports this assumption. This result is in contrast with that of Leah et al. (1991) where an inhibitory effect of ABA on barley acidic chitinase (class III) was observed.

Different regulation patterns of expression for the three classes of chitinase genes and distinct subcellular location of their corresponding enzymes, presumably reflect their different biological functions in the protection of plants against pathogens. Purified chitinases have shown an inhibition of fungal growth (Schlumbaum et al. 1986; Mauch et al. 1988).

Due to its osmotic stress- and ABA-inducible properties, we assume that the acidic chitinase of class II such as the one encoded by pcht28 and pchtI plays a particular role in protecting plants from pathogen attack under stressful environments.

Experimental Procedures

Plant materials.

Seeds of *Lycopersicon chilense* Dun. (LA1930 Peru) were kindly provided by Dr. C. M. Rick (Tomato Genetics Stock Center, University of California, Davis, Calif.). Seedlings were grown in a growth chamber as described previously (Chen and Tabaeizadeh, 1992b). In order to avoid the problem of genetic variability among the plants, one plant (designated as $P_{15}$) was propagated by cutting, and the resulting clones were used for all subsequent experiments.

Cell suspension cultures of *Lycopersicon chilense* were established and maintained as reported previously (Greer and Tabaeizadeh, 1991).

Isolation of cDNA clones. A drought- and ABA-responsive endochitinase cDNA clone pLC15 was selected from a cDNA library of leaves from drought-treated *L. chilense* plants (Chen and Tabaeizadeh, 1992b). $^{32}$P-labelled pLC15 cDNA was used to rescreen the same library for other cDNA clones. The cDNA library was rescreened again with the isolated cDNA clone pchtI as probe.

Nucleotide and amino acid sequence analysis.

Selected cDNAs were subcloned into pSK and completely sequenced in both directions by the dideoxynucleotide chain-termination method (Sanger et al., 1977). Suitable sequencing primers were synthesized on an Applied Biosystems Model 380A synthesizer. Computer analysis of DNA and amino acid sequences was performed using the Wisconsin Genetics Computer Group sequence analysis software package (Devereux et al., 1984). It is understood that, because of the degeneracy of codons, variations in the nucleotidic sequences can occur without modifying the primary structure of the claimed proteins. Such variations are under the scope of this invention.

Experimental treatments.

Plants (45 days after vegetative propagation) were subjected to drought treatment by discontinuing regular watering. Control plants were watered as usual every day. Salt stress was imposed for 4 days by watering 45-day-old plants with half-strength Hoagland solution containing 200 mM NaCl. Exogenous ABA was applied to detached leaves by placing petioles in a solution of 1 mM ABA (Sigma) prepared in 10 mM $NaHCO_3$ for 6 h.

Cultured suspension cells 4 days after sub-culturing were subjected to the different stress treatments for a 24 h period except in the case of heat shock and ABA where exposure times were 0.5 h and 4 h; and 4 h and 24 h, respectively. NaCl, mannitol and ABA treatments were carried out by adding these chemicals into the culture media. Heat shock and cold stress were imposed by incubating suspension cells at 39° C. and 4° C., respectively.

Isolation of DNA and RNA.

Genomic DNA was isolated from etiolated leaves according to Maniatis et al. (1982). Total RNA and poly(A) $^{+}$RNA were isolated as described previously (Chen and Tabaeizadeh 1992b).

Northern and Southern blot analysis.

RNA was denatured with formaldehyde, size-fractionated by electrophoresis in agarose gels, blotted to Hybond-N membranes, and hybridized with $^{32}$P-DNA as described previously (Chen and Tabaeizadeh, 1992b). As a control, the same membrane was rehybridized with rDNA probe from *Coprinus cinereus* (Wu et al., 1983). All samples were shown to have the same quantity of RNA (data not shown). DNA was digested with restriction endonucleases, subjected to agarose gel electrophoresis, blotted to Hybond-N membrane, and hybridized with $^{32}$P-labelled DNAs according to Maniatis et al. (1982). Filters were washed twice at room temperature and once at 65° C. in a buffer containing 0.3×SSPE (20×: 20 mM EDTA, 200 mM $NaH_2HPO_4$ pH 7.5, 3.6M NaCl) and 0.1% SDS.

Expression of Pcht28 in *E. coli* and detection of chitinase activity.

pcht28 cDNA was inserted in frame into EcoR I-Xho I sites within the multiple cloning site of the pBluescript SK⁻ vector (Stratagene). The expression of chitinase protein driven by the lac promoter occurs by depression with 1 mM IPTG in *E. coli* as a chimeric fusion with β-galactosidase (Maniatis et al., 1982). SDS-PAGE was performed to detect chitinase activity according to Trudel and Asselin (1989) with the modification of using 14% polyacrylamide gels. Lytic bands were visualized with transilluminator (UV light) after staining with Calcolfluor White MR2. Proteins from the *E. coli* cells containing pBluescript SK⁻ vector served as controls. A similar expression vector could be obtained using the same above-described strategy, using the same or different restriction enzymes and using, if necessary, synthetic linkers provided that the resulting recombinant plasmid allows for expression of pchtI-encoded chitinase. It is understood that many commercial vectors and cells can be used in this kind of expression assay. As far as the vectors and the recipient cells are compatible to allow for expression of the claimed nucleotide sequences, they are considered to be under the scope of the present invention. Also under the scope of this invention are plasmidic vectors and phages in which propagation and selection of the claimed nucleotidic sequences can be effected.

The invention will be more readily understood by the way of the following Examples and Figures which purpose is not to limit the scope of the invention but rather to illustrate it.

BRIEF DESCRIPTION OF THE FIGURES

FIG. 1. Nucleotide and predicted amino acid sequences of the cDNA clone pcht28 (SEQ ID NO: 1 and SEQ ID NO: 3, respectively) encoding acidic chitinase. Nucleotide positions and amino acid residues are numbered on the right. The putative signal peptide and the polyadenylation signal are underlined. Sequence of the pchtI clone (SEQ ID NO: 2) is shown on the line above the pcht28 sequence with the differences indicated. Differences in the deduced protein sequence (SEQ ID NO: 4) are indicated below the pcht28 protein sequence in parenthesis. The 5' end of the pchtI cDNA is indicated with vertical arrow. Insertions or deletions in the 3' end of the clone are designated by dashes.

FIG. 2. Comparison of the amino acid sequence of pcht28-encoded protein with that of the tobacco acidic endochitinase PR-Q precursor (SEQ ID NO: 5). Homologous amino acids are enclosed in boxes. The signal peptides are underlined.

*chilense*. A: RNA was isolated from cell suspensions cultured in the regular medium (control), and from those subjected to different treatments. NaCl (0.1 and 0.2M), mannitol (200 mM) and cold stress (CS) treatments were carried out for 24 h periods. Cells were exposed to heat shock (HS) treatment at 39° C. for 0.5 h and 4 h. Cold stress was imposed by incubating suspension cells at 4° C. B: RNA was isolated from cell suspensions cultured in the regular maintenance medium (containing 2,4-D), medium without 2,4-D, regular medium containing 20 μM or 100 μM ABA.

Figure 5A:
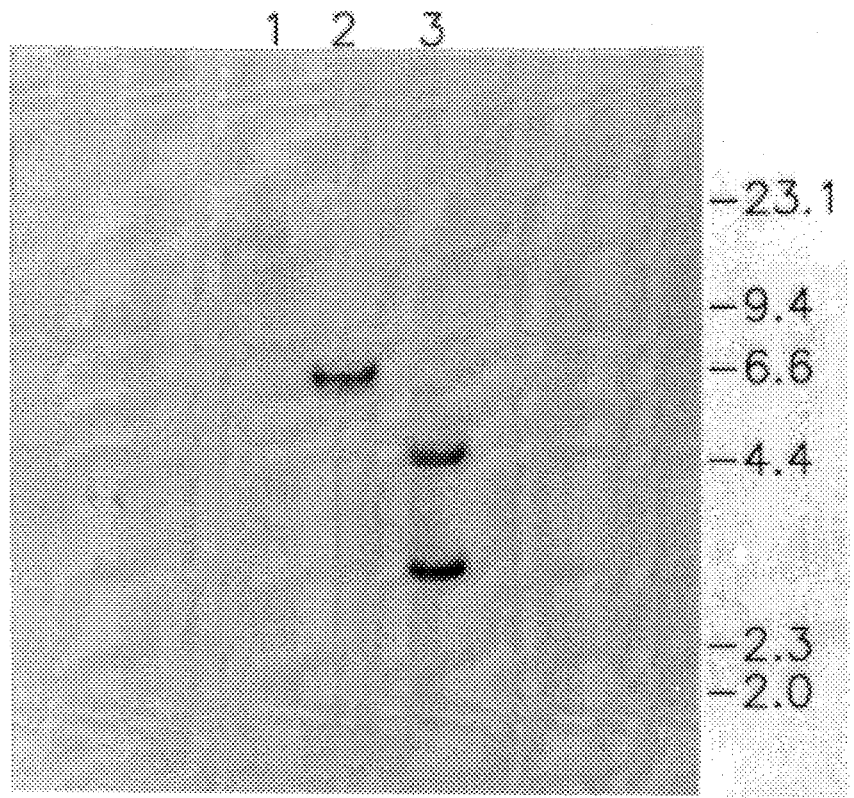
Figure 5B:
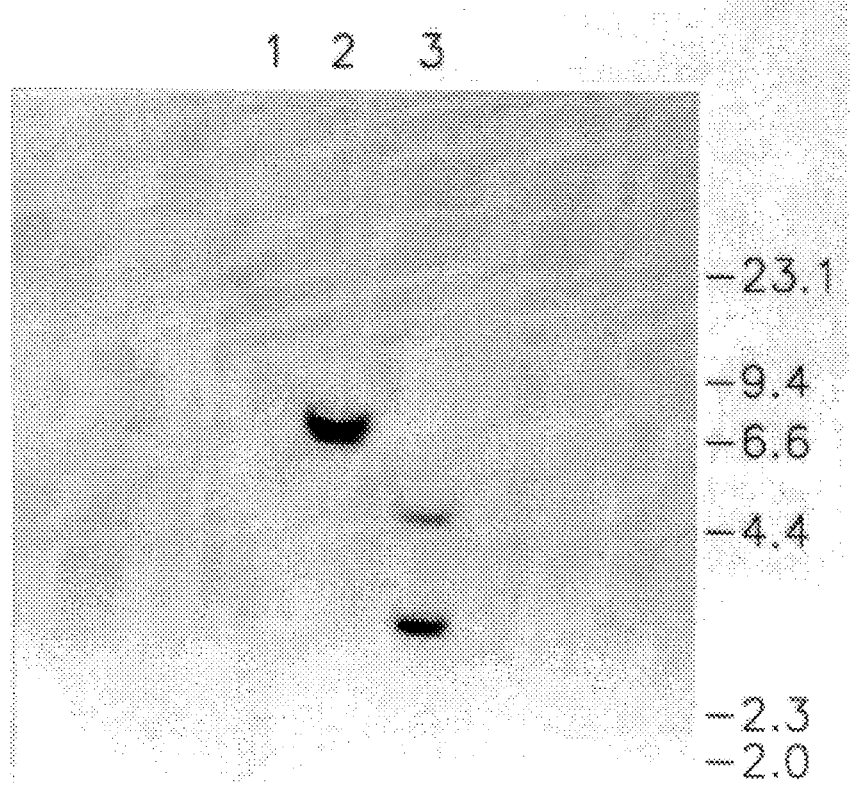

FIGS. 5A and 5B. Southern blot analysis of *L. chilense* genomic DNA. 10 μg of DNA from etiolated leaves were digested with Bam HI (lane 1), Eco RI (lane 2) and Hind III (lane 3), fractionated on a 1% agarose gel, transferred to a Hybond-N membrane and hybridized with the $^{32}$P-labelled cDNA insert of pcht28 (A) or with 3' fragment of Pcht28 (B). Lambda DNA digested with Eco RI and Hind III was included as molecular size standards.

Figure 6:
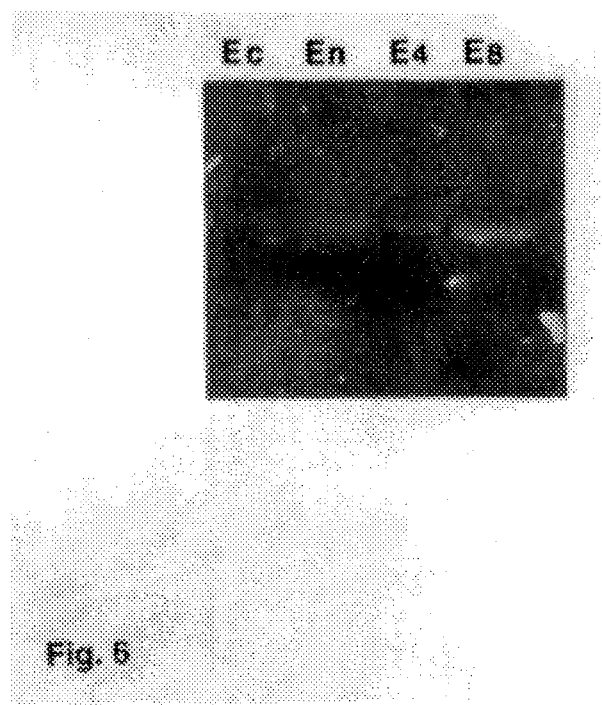

FIG. 6. Chitinase activity assay of the pcht28 protein. Total proteins isolated from *E. coli* were separated on a 14% SDS-polyacrylamide gel containing glycol chitin as substrate. The lytic bands were visualized with transilluminator (UV light) after staining with Calcofluor White MR2. Protein samples correspond to the *E. coli* cells containing pSK$^-$ vector only (Ec), the *E. coli* cells containing pSK$^-$ vector with the insert of pcht28 cDNA without IPTG (En), the *E. coli* cells containing pSK$^-$ vector with the insert of pcht28 cDNA in the presence of 1 mM IPTG for 4 h (E4) and 8 h (E8).

EXAMPLE 1

Isolation of drought- and ABA-induced chitinase cDNAs.

In an attempt to investigate the role of drought and ABA-inducible genes, a cDNA library was prepared in lambda Uni-ZAP XR vector (Stratagene synthesis kit) using poly(A) $^+$RNA prepared from leaves of plants which were drought-stressed for 4 days (Chen and Tabaeizadeh, 1992b). Approximately 10,000 clones of this library were replica plated and differentially screened with cDNA probes prepared from poly(A) $^+$RNA of leaves from control plants, plants subjected to 4 days of drought treatment and plants treated with ABA for 2 days. In total 8 clones preferentially hybridizing with the probes produced from drought- and ABA-treated plants were firstly isolated. The sequence analysis showed that one of these clones, designated as pLC-15, was related to chitinase, sharing 77% amino acid sequence identity with the acidic chitinases PR-P and PR-Q from tobacco (Payne et al., 1990). Because the sequence analysis revealed an incomplete coding sequence, we pursued further for a full-length cDNA clone. Towards this end, 100,000 plaques of the cDNA library were rescreened with $^{32}$P-labelled pLC15 in order to isolate a full-length cDNA clone. Three positive cDNA clones having long inserts were identified. One of them containing the longest insert (designated as pchtI, for chitinase) was characterized. The sequence anlysis showed that this clone was still a partial cDNA. Thus, the 5'-EcoR I-Pst I fragment of the pchtI insert was used as the probe to rescreen 200,000 plaques of the library. Thirty clones which showed strong hybridization signals with pchtI under high-stringency washing conditions were selected and restriction analyzed. Identical to the cDNA insert of pchtI, all of these clones contained 3 internal Pst I sites. The longest cDNA clone, designated as pcht28 (for chitinase), contains an insert of approximately 970 bp. It appeared to be full-length when compared to the size of mRNA revealed by Northern blot, and was selected for further analysis.

EXAMPLE 2

Nucleotide sequence of pcht28 cDNA and its homology to endochitinase

The nucleotide sequence analysis showed that the pcht28 clone contains a full-length cDNA of 966 bp (FIG. 1). The longest open reading frame is 759 bp, corresponding to 253 amino acid residues. A translation initiation codon located at 21 to 23 bp down stream from 5'-end and a translation termination codon is at 780 to 782. A canonical polyadenylation signal (AATAA) is present in the 3' untranslated region 80 nucleotides upstream from the poly(A) tail.

Hydropathy plots highlighted that the protein encoded by pcht28 contains a highly hydrophobic region in the N-terminal sequence, suggesting that it is a secreted protein. It is predicted to have a peptidase signal cleavage site at alanine-glutamine (position 21–22). The mature polypeptide is calculated to have a total molecular weight of 24,943 and is slightly acidic with an estimated pI value of 6.2 and charge of −1.8 at pH 7.0.

The sequence of pchtI is similar to that of pcht28 (FIG. 1). There are four nucleotides different in the coding region due to nucleotide substitution, insertion or deletion. The homologous cDNA clone, pLC15, was also sequenced, and found to be identical to that of pchtI. pchtI and pcht28 are beleived to be isoforms of the same enzyme.

The homology of DNA sequence between pchtI and pcht28 suggests that the first clone obtained, pchtI may contain the whole coding sequence of a chitinase but the first three codons.

Comparison of the deduced protein sequence by computer analysis revealed that the pchtI- and pcht28-encoded proteins share an extensive homology with chitinases from higher plants. The pcht28-encoded protein is remarkably similar to the acidic chitinases from tobacco (FIG. 2) as well as pchtI (data not shown). The mature protein of pcht28 chitinase shares 78% and 77% identity with those of the class II isoforms PR-Q and PR-P from tobacco, respectively (Payne et al., 1990). Alignment of the signal sequences of pcht28 protein with those of PR-Q and PR-P exhibits 66% identity. Moreover, all of them are predicted to be cleaved between an ala/glu junction.

The homology to basic chitinases (class I) was limited to the 3' region (corresponding to amino acids 105 to 253). In this region, it exhibits 60% and 61% identity with basic chitinase precursors from tobacco (Shinshi et al., 1990) and potato (Gaynor, 1988), respectively, suggesting that this region could be the functional domain for enzymatic activity of chitinase.

In contrast, no significant homology was found between the pcht28 protein and acidic chitinases (class III) from cucumber (Metraux et al., 1989) and barley (Leah et al., 1991).

EXAMPLE 3

The expression of pchT28 gene is induced by osmotic stress and ABA

Figure 3A:
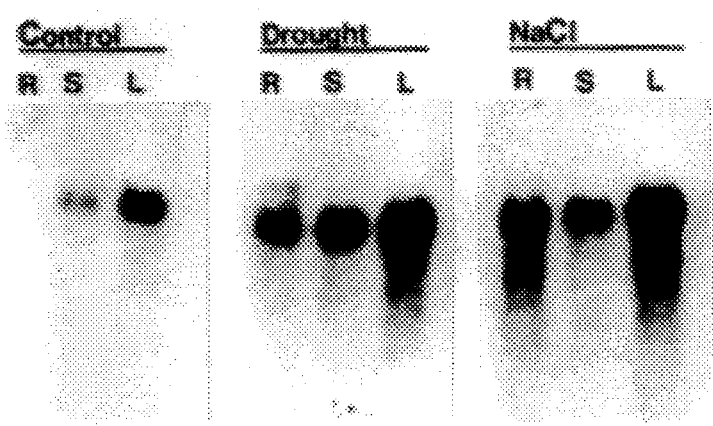
FIGS. 3A and 3B. Northern hybridization analysis of pcht28 gene expression in different organs of intact plants (A) and detached leaves (B). Two µg of total RNA were size-separated on a formaldehyde-1.2% agarose gel, transferred to Hybond-N membranes, and hybridized with $^{32}$P-labelled cDNA insert of pcht28. A: RNA was isolated from roots (R), stems (S) or leaves (L) of plants watered every day as usual (control), plants subjected to water stress for 4 days and plants treated with 200 mM of NaCl for 4 days. B: RNA was extracted from detached leaves treated with 10 mM $NaHCO_3$ (control), air dried (dessication) or 1 mM ABA prepared in 10 mM $NaHCO_3$ solution for 6 h.

Northern blot analysis revealed that pcht28 was organ-specifically expressed in nonstressed plants, showing high levels in leaves and low levels in stems, but was undetectable in roots (FIG. 3A; similar results were obtained for pchtI, not shown). However, a drought treatment of 4 days lead to an accumulation of the mRNA in all three organs, with the highest levels in leaves. A similar induction effect was also observed for plants treated with 200 mM NaCl for 4 days (FIG. 3A), suggesting that this chitinase is osmotic-stress-regulated.

Figures 4A, 4B:
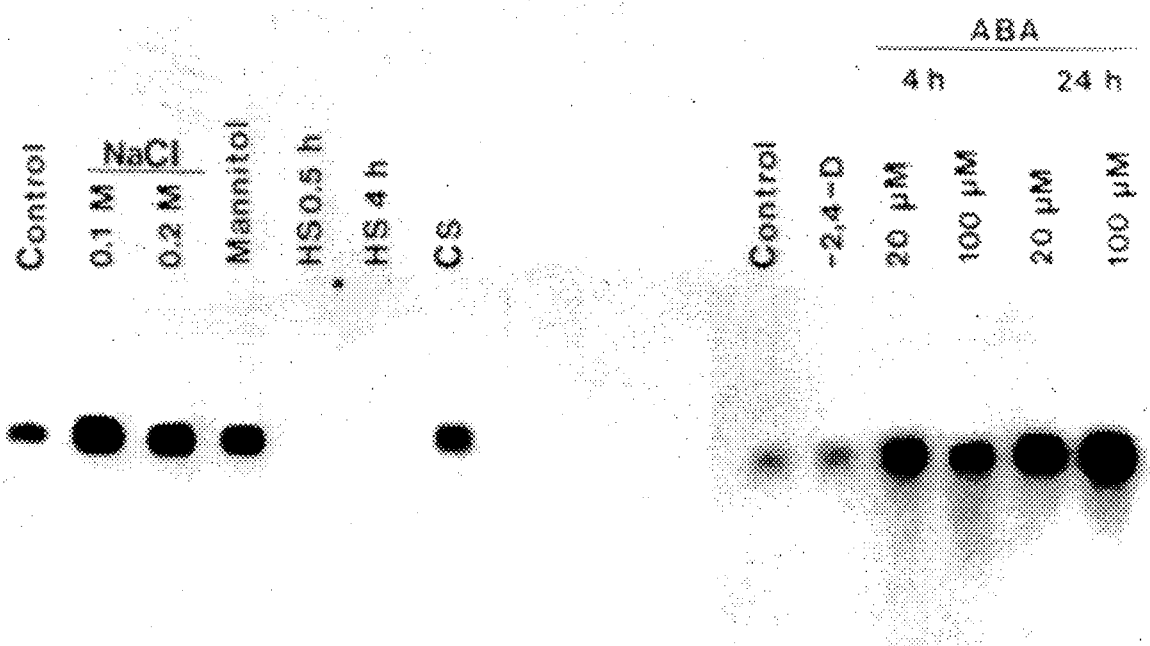
FIGS. 4A and 4B. Northern hybridization analysis of pcht28 gene expression in cultured suspension cells of *L.*

To further confirm the effect of osmotic stress on the expression pattern of the pcht28 gene, cell suspensions of *L. chilense* were also subjected to different treatments (FIG. 4A). The pcht28 gene exhibits a basal level of expression in these cells. Cells remarkably accumulated pcht28 mRNA when subjected to 24-hour periods of NaCl treatment. The expression of the pcht28 gene was also induced by mannitol, a nonionic osmoticum, supporting the hypothesis that the osmotic component of drought treatment is sufficient for pcht28 induction. The expression of the gene was also increased by cold (4° C.) treatment. In contrast, heat shock (39° C.) displayed a strong inhibitory effect on this gene.

Figure 3B:

ABA is generally considered to be the hormone which modulates plant response to drought and salinity stress (Skriver and Mundy, 1990). When this hormone was applied through the cut petiole of detached *L. chilense* leaves, a significant increase in pcht28 gene expression was found, comparing to the control (FIG. 3B; similar results obtained for pchtI, data not shown). In cells cultivated in the presence of ABA (20 or 100 μM), the mRNA levels were up-regulated after 4 h of treatment and continued to increase over a period of 24 h (FIG. 4B). Culture of the cells in the growth medium (Greer and Tabaeizadeh, 1991) with or without 2,4-D did not significantly affect the expression level of pcht28 gene.

EXAMPLE 4

Southern blot analysis of pcht28 gene

To investigate the number of pcht28 genes, genomic DNA was extracted from *L. chilense* and digested with the restriction enzymes BamHI, EcoRI and HindIII. The completely digested DNA was gel electrophoresed and bloted to Hybond N membrane, and then hybridized with full lengthed pcht28 cDNA and the 3'-PstI-XhoI fragment of Pcht28 respectively (FIG. 5). The Pcht28 cDNA hybridized to four BamH1 bands, four Eco RI bands and two Hind III bands. The 3'-fragment hybridized to one BamH1 band, one EcoR1 band and two HindIII bands. These results suggest that there is a small gene family encoding Pcht28 related proteins in *L. chilense*.

EXAMPLE 5

Detection of chitinase activity after SDS-PAGE

The pcht28 protein was expressed in *E. coli* as recombinant protein fused with β-galactosidase at its N-terminus. Total denatured proteins were subjected to SDS-PAGE in 14% polyacrylamide gels containing glycol chitin as the substrate. Chitinase activity was then analyzed after the treatment of the gel in a solution of buffered Triton X-100. FIG. 6 presents the results obtained with the protein samples expressed in *E. coli*. The time course of 0, 4 and 8 hours was used for inducing the expression. A strong band appeared for the cells containing the expression construct after 8 h of induction by IPTG, demonstrating that the pcht28 protein is indeed a chitinase.

EXAMPLE 6

Chitinase activity was measured in *L. chilense* control plants and plants under water stress (data not shown). The activity was remarkably higher in drought treated plants compared to the control plants. Once the drought treated plants were rewatered the activity was reduced almost to the control level.

EXAMPLE 7

Different genotypes of *Lypersicon chilense* Dun. (LA1930 and 2747, Peru) showing different tolerence to fungal pathogens have a positively correlated chitinase activity (data not shown).

The invention has been described herein with reference to certain preferred embodiments. However, as obvious variations thereon will become apparent to those skilled in the art, the invention is not considered limited thereto.

| Symbols for the amino acids | | |
|---|---|---|
| A | Ala | alanine |
| C | Cys | cysteine |
| D | Asp | aspartic acid |
| E | Glu | glumatic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

REFERENCES

Baker, J., Steele, C. & Dure III, L. (1988) Sequence and characterization of 6 Lea proteins and their genes from cotton. *Plant Mol. Biol.* 11, 277–291.

Boller, T. (1989) Ethylene and the regulation of antifungal hydrolases in plants. *Oxf. Surv. Plant Mol. Cell Biol.* 5, 145–174.

Bray, E. A. (1988) Drought-and ABA-induced changes in polypeptide and mRNA in tomato leaves. *Plant. Physiol.* 88, 1210–1214.

Chen, R. D. and Tabaeizadeh, Z. (1992a) Alteration of gene expression in tomato plants (*Lycopersicon esculentum*) by drought and salt stress. *Genome* 35, 385–391.

Chen, R. D. and Tabaeizadeh, Z. (1992b) Expression and molecular cloning of drought-induced genes in the wild tomato *Lycopersicon chilense*. *Biochem. Cell Biol.* 70, 199–206.

Chen, R. D., Campeau N., Greer, A. F., Bellemare G. and Tabaeizmadeh, Z. (1993) Nucleotide sequence of a novel abscissic acid and drought induced gene from the wild tomato *Lycopersicon chilense*. *Plant Physiol.* 103, 301.

Clarke, J. M. and Durley, R. C. (1981) The response of plants to drought stress. In *Water Stress on Plants*, (Simpson, G. M., ed), Praeger, New York, pp. 89–139.

Devereux, J., Hueberli, P. and Smithies, O. (1984) A comprehensive set of sequence analysis program for the VAX. *Nucleic Acids Res.* 12, 387–395

Fisher, R. A. and Turner, N. C. (1978) Plant productivity in the arid and semiarid zones. *Annu. Rev. Plant Physiol.* 29, 277–317.

Gaynor, J. J. (1988) Primary structure of an endochitinase mRNA from *Solanum tuberosum*. *Nucleic Acids Res.* 16, 5210.

Gomez, J., Sanchez-Martinez, D., Stiefel, V., Rigau, J., Puigdomenech, P. and Pages, M. (1988) A gene induced by the plant hormone abscissic acid in response to water stress encodes a glycine-rich protein. *Nature* 334, 262–264.

Greer A. F. and Tabaeizadeh Z. (1991) Characterization and plant regeneration of cell suspension cultures of *Lycopersicon chilense*. *Can. J. Bot.* 69, 2257–2260.

Hanson, A. D. and Hitz, W. D. (1982) Metabolic responses of mesophytes to plant water deficits. *Annu. Rev. Plant Physiol.* 33, 163–203.

Leah, R., Tommerup, H. and Mundy, J. (1991) Biochemical and molecular charactertzation of three barley seed proteins with antifungal properties. *J. Biol. Chem.* 266, 1564–1573.

Maniatis, T., Fritsch, E. P. and Sambrook, J. (1982) *Molecular Cloning: A Laboratory Manual* (Cold Spring Harbor Laboratory, Cold Spring Harbor, N.Y.).

Mauch, F., Mauch-Mani, B., and Boller, T. 1988. Antifungal hydrolases in pea tissue. Inhibition of fungal growth by combinations of chitinase and B-1,3 glucanase. Plant Physiol. 88:936–942.

Memelink, J., Linthorst, H. J. M., Schilperoot, R. A. and Hoge, H. C. (1990) Tobacco genes encoding acidic and basic isoforms of pathogenesis related proteins display different expression patterns. *Plant Mol. Biol.* 14, 119–126.

Metraux, J. P., Burkhart, W. B., Moyer, M., Dincher, S., Middlesteadt, W., Williams, S., Payne, G., Carnes, M. and Ryals, J. (1989) Isolation of a complementary DNA encoding a chitinase with structural homology to a bifunctional lysozyme chitinase. *Proc. Natl. Acad. Sci. USA.* 87, 896–900.

Mundy, J. and Chua N. H. (1988) Abscissic acid and water-stress induce the expression of a novel rice gene. *EMBO J.* 7, 2279–2286.

Neale, A., Wahleithner, J. A., Lund, M., Bonnett, H., Kelly, A., Meeks-Wagner, D. R., Peacock, W. J. and Dennis, E. S. (1990) Chitinase, B-1,3-Glucanase, Osmotin and Extension are expressed in tobacco explants during flower formation. *The Plant Cell.* 2, 673–684.

Parent, J. G., Hogue, R. and Asselin, A. (1985) Glycoproteins enzymatic activities, and b proteins in intercellular fluid extracts from hypersensitive Nicotiana species infected with tobacco mosaic virus. *Can. J. Bot.* 63, 928–931.

Payne, G., Ahl, P., Moyer, M., Harper, A., Beck, J., Meins, F. Jr and Ryals, J. (1990) Isolation of complementary DNA clones encoding pathogenesis-related proteins P and Q, two acidic chitinases from tobacco. *Proc. Natl. Acad. Sci. USA.* 87, 98–102.

Sachs, M. M. and Ho, T. H. D. (1986) Alteration of gene expression during environmental stress in plants. *Annu. Rev. Plant Physiol.* 37, 363–376.

Sanger, F., Nicklen, S. and Coulson A. R. (1977) DNA sequencing with chain terminating inhibitors. *Proc. Natl. Acad. Sci. USA* 83, 5463–5467.

Schlumbaum, A., Mauch, F., Vogeli U., and Boller, T. 1986. Plant chitinases are potent inhibitors of fungal growth. Nature 324:365–367.

Skriver, K. and Mundy, J. (1990) Gene expression response to abscissic acid and osmotic stress. *The Plant Cell* 2, 503–512.

Shinshi, H., Nauhaus, J. H., Ryals, J. and Means K. Fr. (1990) Structure of a tobacco endochitinase gene: Evidence that different chitinase gene can arise by transposition of sequence encoding cysteine-rich domain. *Plant Mol. Biol.* 14, 357–368.

Simpson, G. M. (1981) The value of physiological knowledge of water stress in plants. In *Water Stess on Plants*, (Simpson, G. M., ed), Praeger, New York, pp. 235–265.

Trudel, J. and Asselin A. (1989) Detection of chitinase activity after polyacrylamide gel electrophoresis. *Analytical Biochem.* 178:362–366.

Ward, E. R., Uknes, S. J., Williams, S. C., Dincher, S. S., Wiederhold, D. L., Alexander, D. C., Ahl-Goy, P., Metraux, J. P. and Ryals, J. A. (1991) Coordinate gene activity in response to agents that induce systematic acquired resistance. *The Plant Cell.* 3, 1085–1094.

Wu, M. M. J., Cassisdy, J. R. and Pukkila, P. J. (1983) Polymorphisms in DNA of *Coprinus cinereus*. *Current Genet.* 7, 385–392.

---

What is claimed is:

1. An isolated and purified enzyme which is an endochitinase (EC 3.2.1.14, chitinase) having the amino acid sequence defined in Seq. ID. NO. 2.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 966 base pairs
        ( B ) TYPE: Nucleic Acid
        ( C ) STRANDEDNESS: Single
        ( D ) TOPOLOGY: Linear ( i i ) MOLECULE TYPE: cDNA to mRNA ( v i ) ORIGINAL SOURCE: Lycopersicon chilense ( x i ) SEQUENCE DESCRIPTION: SEQ ID NO: 1:

```
GTTAAAAAGC  CAGAGGAAAA  ATGAAGTTCA  ATATTGTATC  ACCAGTTGCA      50

CTGTCTTGTC  TCTTTTTCTT  GTTCCTAACA  GGTACTTTAG  CACAAAATGC     100

CGGTTCCATT  GTAACGCGGG  AATTGTTCGA  ACAAATGCTG  AGTTTTAGGA     150

ACAATGACGC  ATGTCCTGCC  AAAGGATTCT  ACACTTATGA  TGCATTCATA     200

GCTGCAGCCA  ATTCGTTTCC  AGGTTTTGGT  ACTACTGGTG  ATGATACTGC     250
```

-continued

```
ACGTAAGAAG GAAATTGCTG CCTTTTTCGG TCAAACATCT CATGAAACTA         300

AGGGTGGTAG TGCAGGAACA TTCACTGGAG GATATTGCTT TGTTAGGCAA         350

ATAGATCAGT CAGACAGATA CTATGGCAGA GGACCTATCC AATTGACACA         400

CCAATCTAAC TACGAACGAG CTGGACAAGG TATTGGTGTT GGACAAGACT         450

TAGTGAACAA CCCTGATTTA GTTGCGACAG ATCCTATAAT ATCATTCAGA         500

ACAGCAATAT GGTTCTGGAT GACAGCACAG GATAATAAAC CATCATGCCA         550

CAACGTTATC ATTGGACAAT GGACGCCATC CCCTGCAGAT ACGGCAGCTA         600

ATAGAGTTCC AGGGTACGGT GTCATTACCA ACATCATTAA CGGTGGACTT         650

GAATGTAATA TGGGTCCAAA TACTGCAGTG GAAAGTCGAA TTGGATTTTA         700

CAGGAGGTAT TGTGGTATGT TGAATGTTCC TACTGGTGAA AATTTGGACT         750

GTAACAATCA AAAGAACTTC GCCCAGGGCT AAGCGTCTTT ATATATAGAG         800

AGAATGCAAA TTATGTTTAT GTATTACGTT GTGAAGTCTA TAAGTTATAT         850

TTGGATGTAA TCAATAAGGG GATTCTGTAT GCCCATTTAG AAAAATGGAA         900

GTTGATTTTC AGAAATACTA AAGTTATATG ATTTGATAC TTTTGTTATA         950

AAAAAAAAAA AAAAAA                                             966
```

( 2 ) INFORMATION FOR SEQ ID NO: 2:

( i ) SEQUENCE CHARACTERISTICS:
        ( A ) LENGTH: 253
        ( B ) TYPE: amino acid
        ( D ) TOPOLOGY: unknown ( i i ) MOLECULE TYPE: Protein ( v i ) ORIGINAL SOURCE: Lycopersicon chilense ( x i ) SEQUENCE DESCRIPTION: SEQ ID NO: 2:

```
Met Lys Phe Asn Ile Val Ser Pro Val Ala
                  5                  10

Leu Ser Cys Leu Phe Phe Leu Phe Leu Thr
                 15                  20

Gly Thr Leu Ala Gln Asn Ala Gly Ser Ile
                 25                  30

Val Thr Arg Glu Leu Phe Glu Gln Met Leu
                 35                  40

Ser Phe Arg Asn Asn Asp Ala Cys Pro Ala
                 45                  50

Lys Gly Phe Tyr Thr Tyr Asp Ala Phe Ile
                 55                  60

Ala Ala Ala Asn Ser Phe Pro Gly Phe Gly
                 65                  70

Thr Thr Gly Asp Asp Thr Ala Arg Lys Lys
                 75                  80

Glu Ile Ala Ala Phe Phe Gly Gln Thr Ser
                 85                  90

His Glu Thr Lys Gly Gly Ser Ala Gly Thr
                 95                 100

Phe Thr Gly Gly Tyr Cys Phe Val Arg Gln
                105                 110

Ile Asp Gln Ser Asp Arg Tyr Tyr Gly Arg
                115                 120
```

```
             Gly  Pro  Ile  Gln  Leu  Thr  His  Gln  Ser  Asn
                            125                      130

Tyr  Glu  Arg  Ala  Gly  Gln  Gly  Ile  Gly  Val
                            135                      140

Gly  Gln  Asp  Leu  Val  Asn  Asn  Pro  Asp  Leu
                            145                      150

Val  Ala  Thr  Asp  Pro  Ile  Ile  Ser  Phe  Arg
                            155                      160

Thr  Ala  Ile  Trp  Phe  Trp  Met  Thr  Ala  Gln
                            165                      170

Asp  Asn  Lys  Pro  Ser  Cys  His  Asn  Val  Ile
                            175                      180

Ile  Gly  Gln  Trp  Thr  Pro  Ser  Pro  Ala  Asp
                            185                      190

Thr  Ala  Ala  Asn  Arg  Val  Pro  Gly  Tyr  Gly
                            195                      200

Val  Ile  Thr  Asn  Ile  Ile  Asn  Gly  Gly  Leu
                            205                      210

Glu  Cys  Asn  Met  Gly  Pro  Asn  Thr  Ala  Val
                            215                      220

Glu  Ser  Arg  Ile  Gly  Phe  Tyr  Arg  Arg  Tyr
                            225                      230

Cys  Gly  Met  Leu  Asn  Val  Pro  Thr  Gly  Glu
                            235                      240

Asn  Leu  Asp  Cys  Asn  Asn  Gln  Lys  Asn  Phe
                            245                      250

Ala  Gln  Gly
```

( 2 ) INFORMATION FOR SEQ ID NO: 3:

( i ) SEQUENCE CHARACTERISTICS:
    ( A ) LENGTH: 935 base pairs
    ( B ) TYPE: Nucleic Acid
    ( C ) STRANDEDNESS: Single
    ( D ) TOPOLOGY: Linear ( i i ) MOLECULE TYPE: cDNA to mRNA ( v i ) ORIGINAL SOURCE: Lycopersicon chilense ( x i ) SEQUENCE DESCRIPTION: SEQ ID NO: 3:

```
        AATATTGTAT  CACCAGTTGC  ACTGTCTTGT  CTCTTTTTCT  TGTTCCTAAC      50

AGGTACTTTA  GCACAAAATG  CCGGTTCCAT  TGTAACGCGG  GAATTGTTCG     100

AACAAATGCT  GAGTTTTAGG  AACAATGACG  CATGTCCTGC  CAAAGGATTC     150

TACACTTATG  ATGCATTCAT  AGCTGCAGCC  AATTCGTTTC  AGGTTTTGG      200

TACTACTGGT  GATGATACTG  CACGTAAGAA  GGAAATTGCT  GCCTTTTTCG     250

GTCAAACATC  TCATGAAACT  AATGGTGGTA  GTGCAGGAAC  ATTCACTGGA     300

GGATATTGCT  TTGTTAGGCA  AATAGATCAG  TCAGACAGAT  ACTATGGCAG     350

AGGACCTATC  CAATTGACAC  ACCAATCTAA  CTACGAACGA  GCTGGACAAG     400

GTATTGGTGT  TGGACAAGAC  TTAGTGAACA  ACCCTGATTT  AGTTGCGACA     450

GATCCTATAA  TATCATTCAA  AACAGCAATA  TGGTTCTGGA  TGACAGCACA     500

CCATAATAAA  CCATCATGCC  ACAACGTTAT  CATTGGACAA  TGGACGCCAT     550

CCCCTGCAGA  TACGGCAGCT  AATAGAGTTC  CAGGGTACGG  TGTCATTACC     600
```

|  |  |  |  |  |
|---|---|---|---|---|
| AACATCATTA | ACGGTGGACT | TGAATGTAAT | ATGGGTCCAA | ATACTGCAGT | 650 |
| GGAAAGTCGA | ATTGGATTTT | ACAGGAGGTA | TTGTGGTATG | TTGAATGTTC | 700 |
| CTACTGGTGA | AAATTTGGAC | TGTAACAATC | AAAAGAACTT | CGCCCAGGGC | 750 |
| TAAGCGTCTT | TATATATAGA | GAGAATGCAA | TTATGTTTAT | GTATTACGTT | 800 |
| GTGAAGTCAA | TAAGTTATAT | TTGGATGTAA | TCAATAAGGG | GATTCTGTAT | 850 |
| GCCCATTTAG | AAAAATGGAA | GTTGATTTTC | AGAAATAATA | AAGTTATATG | 900 |
| ATTTTGATCA | TTTTGTTAAA | AAAAAAAAAA | AAAAA |  | 935 |

( 2 ) INFORMATION FOR SEQ ID NO: 4:

( i ) SEQUENCE CHARACTERISTICS:
        ( A ) LENGTH: 250
        ( B ) TYPE: amino acid
        ( D ) TOPOLOGY: unknown ( i i ) MOLECULE TYPE: Protein ( v i ) ORIGINAL SOURCE: Lycopersicon chilense ( x i ) SEQUENCE DESCRIPTION: SEQ ID NO: 4:

```
Asn Ile Val Ser Pro Val Ala Leu Ser Cys
              5                      10

Leu Phe Phe Leu Phe Leu Thr Gly Thr Leu
             15                      20

Ala Gln Asn Ala Gly Ser Ile Val Thr Arg
             25                      30

Glu Leu Phe Glu Gln Met Leu Ser Phe Arg
             35                      40

Asn Asn Asp Ala Cys Pro Ala Lys Gly Phe
             45                      50

Tyr Thr Tyr Asp Ala Phe Ile Ala Ala Ala
             55                      60

Asn Ser Phe Pro Gly Phe Gly Thr Thr Gly
             65                      70

Asp Asp Thr Ala Arg Lys Lys Glu Ile Ala
             75                      80

Ala Phe Phe Gly Gln Thr Ser His Glu Thr
             85                      90

Asn Gly Gly Ser Ala Gly Thr Phe Thr Gly
             95                     100

Gly Tyr Cys Phe Val Arg Gln Ile Asp Gln
            105                     110

Ser Asp Arg Tyr Tyr Gly Arg Gly Pro Ile
            115                     120

Gln Leu Thr His Gln Ser Asn Tyr Glu Arg
            125                     130

Ala Gly Gln Gly Ile Gly Val Gly Gln Asp
            135                     140

Leu Val Asn Asn Pro Asp Leu Val Ala Thr
            145                     150

Asp Pro Ile Ile Ser Phe Lys Thr Ala Ile
            155                     160

Trp Phe Trp Met Thr Ala His His Asn Lys
            165                     170

Pro Ser Cys His Asn Val Ile Ile Gly Gln
```

|     |     |     |     | 175 |     |     |     |     | 180 |
|---|---|---|---|---|---|---|---|---|---|
| Trp | Thr | Pro | Ser | Pro | Ala | Asp | Thr | Ala | Ala |
|     |     |     |     | 185 |     |     |     |     | 190 |
| Asn | Arg | Val | Pro | Gly | Tyr | Gly | Val | Ile | Thr |
|     |     |     |     | 195 |     |     |     |     | 200 |
| Asn | Ile | Ile | Asn | Gly | Gly | Leu | Glu | Cys | Asn |
|     |     |     |     | 205 |     |     |     |     | 210 |
| Met | Gly | Pro | Asn | Thr | Ala | Val | Glu | Ser | Arg |
|     |     |     |     | 215 |     |     |     |     | 220 |
| Ile | Gly | Phe | Tyr | Arg | Arg | Tyr | Cys | Gly | Met |
|     |     |     |     | 225 |     |     |     |     | 230 |
| Leu | Asn | Val | Pro | Thr | Gly | Glu | Asn | Leu | Asp |
|     |     |     |     | 235 |     |     |     |     | 240 |
| Cys | Asn | Asn | Gln | Lys | Asn | Phe | Ala | Gln | Gly |
|     |     |     |     | 245 |     |     |     |     | 250 |

(2) INFORMATION FOR SEQ ID NO: 5:

(i) SEQUENCE CHARACTERISTICS:
  (A) LENGTH: 253
  (B) TYPE: amino acid
  (D) TOPOLOGY: unknown (ii) MOLECULE TYPE: Protein (vi) ORIGINAL SOURCE: Nicotiana tabacum (xi) SEQUENCE DESCRIPTION: SEQ ID NO: 5:

|     |     |     |     |     |     |     |     |     |     |
|---|---|---|---|---|---|---|---|---|---|
| Met | Glu | Phe | Ser | Gly | Ser | Pro | Met | Ala | Leu |
|     |     |     |     | 5   |     |     |     |     | 10  |
| Phe | Cys | Cys | Val | Phe | Phe | Leu | Phe | Leu | Thr |
|     |     |     |     | 15  |     |     |     |     | 20  |
| Gly | Ser | Leu | Ala | Gln | Gly | Ile | Gly | Ser | Ile |
|     |     |     |     | 25  |     |     |     |     | 30  |
| Val | Thr | Ser | Asp | Leu | Phe | Asn | Glu | Met | Leu |
|     |     |     |     | 35  |     |     |     |     | 40  |
| Lys | Asn | Arg | Asn | Asp | Gly | Arg | Cys | Pro | Ala |
|     |     |     |     | 45  |     |     |     |     | 50  |
| Asn | Gly | Phe | Tyr | Thr | Tyr | Asp | Ala | Phe | Ile |
|     |     |     |     | 55  |     |     |     |     | 60  |
| Ala | Ala | Ala | Asn | Ser | Phe | Pro | Gly | Phe | Gly |
|     |     |     |     | 65  |     |     |     |     | 70  |
| Thr | Thr | Gly | Asp | Asp | Thr | Ala | Arg | Arg | Lys |
|     |     |     |     | 75  |     |     |     |     | 80  |
| Glu | Ile | Ala | Ala | Phe | Phe | Gly | Gln | Thr | Ser |
|     |     |     |     | 85  |     |     |     |     | 90  |
| His | Glu | Thr | Thr | Gly | Gly | Ser | Leu | Ser | Ala |
|     |     |     |     | 95  |     |     |     |     | 100 |
| Glu | Pro | Phe | Thr | Gly | Gly | Tyr | Cys | Phe | Val |
|     |     |     |     | 105 |     |     |     |     | 110 |
| Arg | Gln | Asn | Asp | Gln | Ser | Asp | Arg | Tyr | Tyr |
|     |     |     |     | 115 |     |     |     |     | 120 |
| Gly | Arg | Gly | Pro | Ile | Gln | Leu | Thr | Asn | Arg |
|     |     |     |     | 125 |     |     |     |     | 130 |
| Asn | Asn | Tyr | Glu | Lys | Ala | Glu | Thr | Ala | Ile |
|     |     |     |     | 135 |     |     |     |     | 140 |
| Gly | Gln | Glu | Leu | Val | Asn | Asn | Pro | Asp | Leu |

|     |     |     |     | 145 |     |     |     |     | 150 |
|-----|-----|-----|-----|-----|-----|-----|-----|-----|-----|
| Val | Ala | Thr | Asp | Ala | Thr | Ile | Ser | Phe | Lys |
|     |     |     |     | 155 |     |     |     |     | 160 |
| Thr | Ala | Ile | Trp | Phe | Trp | Met | Thr | Pro | Gln |
|     |     |     |     | 165 |     |     |     |     | 170 |
| Asp | Asn | Lys | Pro | Ser | Ser | His | Asp | Val | Ile |
|     |     |     |     | 175 |     |     |     |     | 180 |
| Ile | Gly | Arg | Trp | Thr | Pro | Ser | Ala | Ala | Asp |
|     |     |     |     | 185 |     |     |     |     | 190 |
| Gln | Ala | Ala | Asn | Arg | Val | Pro | Gly | Tyr | Gly |
|     |     |     |     | 195 |     |     |     |     | 200 |
| Val | Ile | Thr | Asn | Ile | Ile | Asn | Gly | Gly | Ile |
|     |     |     |     | 205 |     |     |     |     | 210 |
| Glu | Cys | Gly | Ile | Gly | Arg | Asn | Asp | Ala | Val |
|     |     |     |     | 215 |     |     |     |     | 220 |
| Glu | Asp | Arg | Ile | Gly | Tyr | Tyr | Arg | Arg | Tyr |
|     |     |     |     | 225 |     |     |     |     | 230 |
| Cys | Gly | Met | Leu | Asn | Val | Ala | Pro | Gly | Glu |
|     |     |     |     | 235 |     |     |     |     | 240 |
| Asn | Leu | Asp | Cys | Tyr | Asn | Gln | Arg | Asn | Phe |
|     |     |     |     | 245 |     |     |     |     | 250 |
| Gly | Gln | Gly |     |     |     |     |     |     |     |